(12) United States Patent
Gedeon et al.

(10) Patent No.: US 8,457,989 B2
(45) Date of Patent: Jun. 4, 2013

(54) DIRECT REPORTING OF ADVERSE EVENTS

(75) Inventors: Hanna Mina Gedeon, Lenexa, KS (US); Sara Jane Griffin, Lees Summit, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 575 days.

(21) Appl. No.: 12/351,620

(22) Filed: Jan. 9, 2009

(65) Prior Publication Data

US 2010/0179829 A1    Jul. 15, 2010

(51) Int. Cl.
*G06Q 50/00* (2012.01)
(52) U.S. Cl.
USPC .................................. 705/3; 705/2
(58) Field of Classification Search
USPC ................... 707/100, 636; 705/2, 3
See application file for complete search history.

(56) References Cited

U.S. PATENT DOCUMENTS

| | | | |
|---|---|---|---|
| 6,122,671 A | 9/2000 | Farrar et al. | |
| 2002/0138605 A1 | 9/2002 | Hole | |
| 2004/0093240 A1 | 5/2004 | Shah | |
| 2006/0014945 A1 | 1/2006 | Galley et al. | |
| 2006/0036619 A1* | 2/2006 | Fuerst et al. | 707/100 |
| 2006/0178910 A1* | 8/2006 | Eisenberger et al. | 705/3 |
| 2008/0104613 A1 | 5/2008 | Ciszkowski et al. | |
| 2008/0220726 A1 | 9/2008 | Gulati et al. | |
| 2009/0191608 A1 | 7/2009 | Matsumoto | |
| 2011/0029488 A1* | 2/2011 | Fuerst et al. | 707/636 |

OTHER PUBLICATIONS

The Sentinel Initiative National Strategy for Monitoring Medical Product Safety, May 2008; FDA; Department of Health and Human Services; U.S. Food and Drug Administration Office of Critical Path Programs www.fda.gov/oc/initiatives/criticalpath/.
The Aster Project: Improving the Reporting of Adverse Events and Making Spontaneous Reporting Work: Sep. 3, 2008; Michael Ibara, Head of Pharmacovigilence Information Management @ Pfizer.
NonFinal Office Action mailed 12/21/2010, U.S. Appl. No. 12/351,628, 14 pages.
Final Office Action mailed Apr. 25, 2011, U.S. Appl. No. 12/351,628.

* cited by examiner

*Primary Examiner* — Valerie Lubin
(74) *Attorney, Agent, or Firm* — Shook Hardy & Bacon LLP

(57) ABSTRACT

Systems, methods, and computer readable media are described for communicating an adverse event report directly to an end-user receiving party and tracking one or more adverse event reports. An adverse event may be detected manually or automatically by a system and an electronic adverse event reporting form presented to a user with one or more data fields pre-populated with data from a patient's electronic health record (EHR). The user may enter and edit data in the electronic form and may submit the data in the electronic form directly to an end-user receiving party such as the U.S. Food and Drug Administration. One or more receipts may be received from the receiving party and indicia from the receipts recorded to one or more records. The submitted adverse event reports may be tracked, accessed, and interacted with through a user interface and additional information may be provided to a user therein.

17 Claims, 12 Drawing Sheets

| BRADY, HOPE | | | | |
|---|---|---|---|---|
| BRADY, HOPE | DOB:9/18/1961 | EMR:00001352 | FIN #:000001447 | |
| ** ALLERGIES ** | AGE:47 YEARS | GENDER:FEMALE | LOC:MER-ED ;3B | |

| MENU | |
|---|---|
| ORDERS + ADD | ADVERSE EVENT REPORT |
| RECENT RESULTS | 🏠 ▫▫▫▫ 100% ▾ |
| VITAL SIGNS | ADVERSE EVENT REPORT |
| LAB | * REQUIRED INFORMATION |
| RADIOLOGY | ⦿ NEW ○ EXISTING REPORTS |
| ASSESSMENTS | [+] PATIENT INFORMATION |
| I-VIEW POWER | |
| HISTORIES | [+] ADVERSE EVENT, PRODUCT PROBLEM OR ERROR* |
| FORM BROWSER | |
| INFORMATION | [+] PRODUCT AVAILABILITY |
| MEDICATION | |
| 24 HR PHYS. | [+] SUSPECT/CONCOMITANT PRODUCT(S) |
| 72 HR PHYS. | |
| ONCOLOGY | [+] SUSPECT MEDICAL DEVICE |
| MAR | |
| MEDICATION | [+] INITIAL REPORTER (SUBMISSION OF A REPORT DOES NOT CONSTITUTE AN ADMISSION THAT M... |
| PROBLEMS | |
| TASK LIST | |
| FLUID BALANCE | |
| FALL RISK | |
| PATIENT CARE | |
| PRENATAL | |
| ADVANCED | |
| ACQUIRED DATA | |

*FIG. 9.*

ADVERSE EVENT REPORT

ADVERSE EVENT REPORT
*REQUIRED INFORMATION
⦿ NEW  ○ EXISTING REPORTS

[+] PATIENT INFORMATION

[-] ADVERSE EVENT, PRODUCT PROBLEM OR ERROR*

1. CHECK ALL THAT APPLY:
   ☐ ADVERSE EVENT
   ☐ PRODUCT PROBLEM (E.G., DEFECTS/MALFUNCTIONS)
   ☐ PRODUCT USE ERROR
   ☐ PROBLEM WITH DIFFERENT MANUFACTURER OF SAME MEDICINE

2. OUTCOMES ATTRIBUTED TO ADVERSE EVENT (CHECK ALL THAT APPLY):
   ☐ DEATH  [//****]
   ☐ DISABILITY OR PERMANENT DAMAGE
   ☐ LIFE-THREATENING
   ☑ CONGENITAL ANOMALY/BIRTH DEFECT
   ☑ HOSPITALIZATION – INITIAL OR PROLONGED
   ☐ OTHER SERIOUS (IMPORTANT MEDICAL EVENTS)
   ☐ REQUIRED INTERVENTION TO PERMANENT IMPAIRMENT/DAMAGE (DEVICES)

3. DATE OF EVENT:          10/13/2008

4. DATE OF THIS REPORT:    10/15/2008

5. DESCRIBE EVENT, PROBLEM, OR PRODUCT USE ERROR *(REQUIRED)

6. RELEVANT TESTS/LABORATORY DATA, INCLUDING DATES

09/22/2008 15:41:  HEMOGRAM = 455
   09/22/2008 15:41:  HEP_FUNC PANEL = 99 UNIT/L
   09/27/2008 15:24:  CREATININE = 1.0 MG/DL
   09/27/2008 15:24:  LYTES = 12MEQ/L

ADVERSE EVENT REPORT

◀ ☐ ☐ ☐ ☐ | 100% ▼ |

ADVERSE EVENT REPORT
* REQUIRED INFORMATION
● NEW  ○ EXISTING REPORTS

[+] PATIENT INFORMATION

[+] ADVERSE EVENT, PRODUCT PROBLEM OR ERROR*

[−] PRODUCT AVAILABILITY

PRODUCT AVAILABLE FOR EVALUATION?  ● YES  ○ NO
☐ RETURNED TO MANUFACTURE ON: [//****]

[−] SUSPECT/CONCOMITANT PRODUCT(S)

[ ADD PRODUCT(S)... ]

| TURNS E-X ▶ | [ REMOVE ROW ] |
|---|---|
| CHARACTERIZATION: | ● SUSPECT ○ CONCOMITANT ○ INTERACTING |
| MANUFACTURER: | |
| STRENGTH: | 1500  MG |
| DOSE OR AMOUNT: | |
| FREQUENCY: | Q1HR |
| ROUTE | CHEWED |
| START DATE/TIME: | 05/01/08 11:06:00 CDT |
| DURATION: | |
| END DATE/TIME: | |
| REASON FOR USE: | |
| DIAGNOSIS: | |
| EVENT ABATED AFTER USE STOPPED OR DOSE REDUCED | ● YES  ○ NO  ○ DOES NOT APPLY |
| EXPIRATION DATE: | //**** |
| EVENT REAPPEARED AFTER REINTRODUCTION: | ● YES  ○ NO  ○ DOES NOT APPLY |
| NDC # OR UNIQUE ID: | |
| OTHER: | |

ADVERSE EVENT REPORT

□□□□ 100% ▾

ADVERSE EVENT REPORT
* REQUIRED INFORMATION
◉ NEW   ○ EXISTING REPORTS

[+] PATIENT INFORMATION

[+] ADVERSE EVENT, PRODUCT PROBLEM OR ERROR*

[+] PRODUCT AVAILABILITY

[+] SUSPECT/CONCOMITANT PRODUCT(S)

[−] SUSPECT MEDICAL DEVICE

1. BRAND NAME:
2. COMMON DEVICE NAME:
3. MANUFACTURER NAME:    CITY:   STATE: [SELECT ▾]
4. MODEL:   CATALOG:
   SERIAL NUMBER:   LOT: [//****]   OTHER:
   EXPIRATION DATE: [   ]
5. OPERATOR OF DEVICE: ○ HEALTH PROFESSIONAL ○ PATIENT ○ OTHER
6. IF IMPLANTED, GIVE DATE: [//****]
7. IF EXPLANTED, GIVE DATE: [//****]
8. IS THIS A SINGLE-USE DEVICE THAT WAS REPROCESSED AND REUSED ON A PAITENT?

[−] INITIAL REPORTER (SUBMISSION OF A REPORT DOES NOT CONSTITUTE AN ADMISSION THAT M....
* (AT LEAST ONE OF THE FOLLOWING IS REQUIRED: INITIALS/NAME, ADDRESS, QUALIFICATION.)

1. NAME: [JIM JENSEN]   ADDRESS: [1255 SIGMA PKWY, KANSAS CITY MO 64127]
   PHONE: [(816) 113-0007]   E-MAIL: [JJENSEN@EMAIL.COM]
2. HEALTH PROFESSIONAL: ◉ YES ○ NO
3. OCCUPATION: [DBA NO DTA]
4. ALSO REPORTED TO: □ MANUFACTURER □ USER FACILITY □ DISTRIBUTOR/IMPORTER □ FDA
5. □ CHECK THIS BOX IF YOU DO NOT WANT YOUR IDENTITY DISCLOSED TO THE MANUFACTURE.

[SUBMIT] [SAVE] [RESET]

ADVERSE EVENT REPORTS ORGANIZER FOR J. JENSEN

| PATIENT LIST | PATIENT ACCESS LIST | MULTI-PATIENT TASK LIST | IN-BOX |

ADVERSE EVENT REPORT

| PATIENT NAME | ADVISOR TYPE | ADVISOR STATUS | ADVISOR DESCRIPTION |
|---|---|---|---|
| BELANGER, HUGO | | | PATIENT HAD ADVERSE EVENT WHEN TAKING HYDROCODONE |
| BERGERON, PATRICE F. | | | FELL DOWN FROM MACHINE |
| | | | FELL DOWN FROM MACHINE |
| | | | PT – FIST WENT THROUGH THE DEVICE CAUSING NERVE... |
| | | | ALLERGIC RXN TO OTC PAIN KILLER |
| | | | PATIENT SUFFERING FROM HIVES CAUSED BY CREAM... |
| | | | RASH AT INJECTION SITE |
| | | | BED RAIL MALFUNCTION CAUSED PATIENT TO FALL FROM... |
| | | | THE DEVICE RPM'S PICKED UP SPEED CAUSING VENTILATOR |
| BIRON, MARTIN | | | DEVICE WAS AT FAULT, PT FELL AND REINJURE KNEE |
| BRADY, HOPE | | | ALLERGIC RXN TO MEDICAL TAPE |
| BRISEBOIS, PATRICE | | | PATIENT SUFFERED SEIZURE AFTER INJECTION OF ... |
| | | | PATIENT SUFFERED STROKE AFTER STRESS TEST EVAL... |
| | | | RXN TO PAIN KILLER CAUSED INTERNAL BLEEDING |
| | | | ADVERSE EVENT WITH THE TRACHEA TUBE OCCURRED... |
| | | | ADVERSE EVENT OCCURRED WHEN PATIENT WAS GIVEN... |
| CAMP, JEREMY F. | | | VENTILATOR CAUSED TROUBLE BREATHING |
| CONSTANTINE, KEVIN J. | | | INCORRECT INSULIN DOSAGE GIVEN |
| | | | URINE KETONES AS A RESULT FROM DEXTROSE IV |
| JACKSON, MILES | | | PACEMAKER MALFUNCTION |
| | | | PT SUFFERED CHEMICAL BURN AT APPLICATION SITE OF... |
| | | | INTERNAL BLEEDING AT INCISION SITE |
| | | | ALLERGIC RXN TO SUTURES |

*FIG. 14.*

DIRECT REPORTING OF ADVERSE EVENTS

CROSS-REFERENCE TO RELATED APPLICATIONS

This application is related by subject matter to the invention disclosed in the commonly assigned application filed concurrently herewith: entitled "TRACKING DIRECT REPORTED ADVERSE EVENTS" Ser. No. 12/351,628. The disclosure of the aforementioned application is hereby incorporated by reference in its entirety.

BACKGROUND

In the healthcare setting, an adverse event may be described generally, as a situation involving harm or potential harm to a patient or an adverse reaction of a patient to care provided. An adverse event may include an adverse reaction to a drug or combination of drugs, an adverse drug event, a drug-to-drug interaction, a medication error, a side effect of a drug or drugs, a medical error, or other non-drug related events. An adverse event may also be linked to medical devices employed in patient care.

Regulatory bodies, government and non-government organizations, as well as manufacturers are interested in adverse events for the purpose of ongoing tracking, surveillance or research. Certain types of adverse events, if reported, are reported on a voluntary basis by patients, caregivers, and/or clinicians via a paper based form system. A clinician, upon identification of an adverse event, voluntarily fills out an adverse event form and submits the form to the proper regulatory agency, or other interested parties. Such a system has historically been found to produce reporting rates of less than ten percent due to several possible factors including the difficulty in identifying the occurrence of an adverse event, the hindrance on busy medical personnel's time and workflow, and the lack of value to medical personnel in reporting.

SUMMARY

This summary is provided to introduce a selection of concepts in a simplified form that are further described below in the Detailed Description. This summary is not intended to identify key features or essential features of the claimed subject matter, nor is it intended to be used in isolation as an aid in determining the scope of the claimed subject matter.

Embodiments of the invention generally relate to methods, systems, and computer readable media for electronically reporting and tracking adverse event reports to regulatory bodies, as well as other government organizations, manufacturers, and non-governmental organizations, among others. Accordingly, in one aspect, the invention provides a method in a clinical computing environment for communicating data in an electronic adverse event reporting form directly to one or more end-user receiving parties. An electronic form is pre-populated with one or more data and provided to a user for further data entry. The data in the electronic form are then communicated to a regulatory body, among other possible recipients.

In a further aspect of the invention, the adverse event report communicated via the electronic adverse event reporting form is tracked. One or more receipts may be received from a recipient of the data in the electronic form and indicia of the receipt recorded in one or more corresponding records. The status of the adverse event report is queried and a user provided with a user interface to view and interact with data corresponding to one or more adverse event reports.

Additional objects, advantages, and novel features of embodiments of the invention will be set forth in part in the description that follows, and in part will become apparent to those skilled in the art upon examination of the following, or may be learned by practice of the invention.

BRIEF DESCRIPTION OF THE DRAWING

Illustrative embodiments of the invention are described in detail below with reference to the attached drawing figures, wherein:

FIG. 9 is a graphical representation of an electronic adverse event reporting form according to an embodiment of the invention;

FIG. 11 is a graphical representation of an adverse event section of an electronic adverse event reporting form according to an embodiment of the invention;

FIG. 12 is a graphical representation of a product availability and suspect/concomitant product section of an electronic adverse event reporting form according to an embodiment of the invention;

FIG. 13 is a graphical representation of a suspect medical device section of an electronic adverse event reporting form according to an embodiment of the invention; and FIG. 14 is a graphical representation of an adverse event reports tracking display according to an embodiment of the invention.

DETAILED DESCRIPTION

Figure 1:
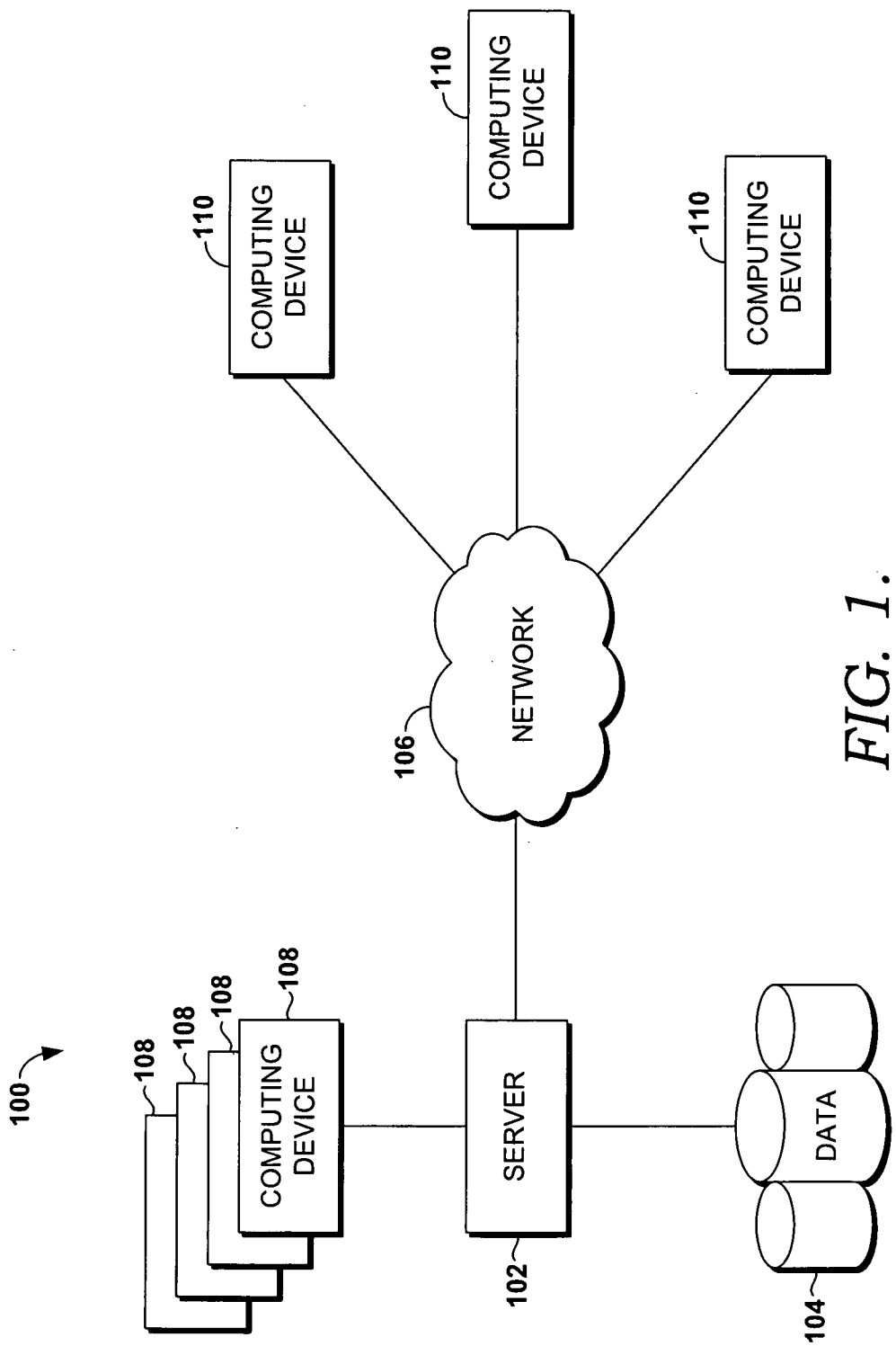
FIG. 1 is a block diagram of an exemplary computing environment suitable for use in implementing embodiments of the invention.

The subject matter of embodiments of the invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the invention provide methods, systems, and computer-readable media for electronically submitting adverse event reports directly to end-user receiving parties such as regulatory bodies, as well as other government organizations, manufacturers, and non-governmental organizations, among others. Embodiments of the invention also provide methods, systems, and computer-readable media for tracking adverse event reports reported to end-user receiving parties.

The receiving parties may be described as "end-user" receiving parties in that no third party is involved in the communication of the data in the electronic form between a user's computing system and the final receiving party other than that necessary for enabling communication over a network. For example, the data in an electronic form are sent directly to the receiving party rather than to an intervening third party that re-formats and encrypts the form, among other operations, and then forwards the form to the receiving party.

Regulatory bodies may comprise, for instance, any governmental or non-governmental body tasked with regulating healthcare in the United States, Europe or otherwise, and may include the United States Food and Drug Administration (FDA) and the European Medicines Agency (EMEA), among others. Government agencies, non-governmental health organizations, research groups, and interested parties may include any group wishing to receive adverse event reports for research, compilation, tracking, or other uses. Manufacturers may include manufacturers of a drug, biologic, nutritional supplement, device, or similar product that wish to be notified or that require such notifications.

An adverse event may be described generally, as a situation involving harm or potential harm to a patient or an adverse reaction of a patient to care provided. Adverse events may have various results ranging from the most minor, such as a rash, abrasion, or minor illness to the most serious including death. Adverse events are often categorized based on the severity of the outcome. Adverse reactions may occur as a patient reaction to a drug, a drug-to-drug interaction, an adverse drug reaction, a medication error, or a side effect, among other drug related events. An adverse event may also occur as a result of inappropriate use or an adverse reaction of a patient to a device, such as, for example, an implant, traction equipment, or rehabilitation equipment, among others. Adverse events may also occur as a result of other non-drug related events or medical errors.

Reporting of adverse events potentially related to drugs, biologics, nutritional supplements, and medical devices is required by government organizations and regulatory bodies during clinical trials, but may be voluntary for medical personnel and healthcare organizations once products are in general use. Reporting and compiling adverse events on a large scale such as the medical community as a whole may provide valuable data and a positive contribution to the knowledge base for administration and development of medical products. Further, providing medical personnel with information related to and compiled from adverse event reports may increase the quality and safety of patient care.

In one aspect of the invention, a method in a clinical computing environment for communicating data in an electronic adverse event reporting form directly to end-user receiving parties is disclosed. An electronic adverse event reporting form pre-populated with data is presented on a display. Additional data are received from a user. The data in the electronic form are communicated to the end-user receiving parties, wherein the end-user receiving parties may include a government organization, a regulatory agency, a manufacturer, a non-governmental health organization, a research organization, quality control personnel, or other interested parties.

In another aspect of the invention, a system in a clinical computing environment for facilitating the direct communication of data in an electronic adverse event reporting form to end-user receiving parties is described. The system includes an adverse event detection component for detecting an adverse event through monitoring and analyzing a patient's electronic health records or by receiving a user input. The system also includes an electronic form generation component for generating an electronic form, pre-populating the form with data from electronic records, and presenting the pre-populated form to a user to allow data input. The system further includes a communication component for communicating the data in the electronic form directly to the end-user receiving parties.

In another aspect of the invention, a method in a clinical computing environment for communicating data in an electronic adverse event reporting form directly to end-user receiving parties is described. The occurrence of an adverse event is detected automatically by monitoring and analyzing a patient's electronic health record or manually by receiving an input from a user. A user is prompted to complete an electronic adverse event reporting form when an adverse event is automatically detected. An electronic adverse event reporting form is pre-populated with data from a patient's electronic health record. The electronic form is presented to a user on a display. Additional data inputs are received from a user to the electronic form. The electronic form is prepared for communicating to the United States Food and Drug Administration by formatting the data in the electronic form in an electronic messaging format in compliance with a Health Level Seven, Inc. (HL7) standard and International Conference on Harmonization of Technical Requirements for Registration of Pharmaceuticals for Human Use (ICH) guidelines. Validation, encryption and signing of the message are also provided. The data are communicated to the FDA as an electronic mail message.

In a further aspect of the invention, a method in a clinical computing environment for tracking adverse event reports is described. Data in electronic adverse event reporting forms are communicated to end-user receiving parties. Received receipts are received from the end-user receiving parties for each of the communicated electronic forms. Indicia corresponding to the received receipts are recorded in records associated with the communicated electronic forms. The status of adverse event reports communicated to the end-user receiving parties as an electronic form is queried. A user interface is provided on a display to allow a user to view, query, audit, and create reports for data corresponding to the adverse event reports.

In yet a further aspect of the invention, a system in a clinical computing environment for facilitating the tracking of adverse event reports is disclosed. The system includes a communication component for communicating data in an electronic adverse event reporting forms to end-user receiving parties. The system also includes a receiving component for receiving an acknowledgement receipt, a successful transmission receipt, a transmission failure receipt, and a unique identifier for each communicated electronic form. The system further includes a recording component for recording the receipts and identifiers received by the receiving component in records associated with each of the adverse event reports, and a displaying component for presenting on a display data corresponding to the adverse event reports.

In yet another aspect of the invention, a method in a clinical computing environment for tracking adverse event reports is described. Data in electronic adverse event reporting forms are communicated to end-user receiving parties as an electronic mail message. An acknowledgment receipt is received for each of the communicated electronic forms. A successful transmission receipt and a transmission failure receipt for each of the communicated electronic forms is received. A unique identifier for each of the electronic forms is received from the end-user receiving parties. Indicia corresponding to the acknowledgment receipt, the successful transmission receipt or transmission failure receipt, and the unique identifier are recorded in records associated with the communicated electronic forms. The status of adverse event reports communicated to the end-user receiving parties as an electronic form is queried. A user interface is provided on a display to allow a user to view, query, audit, and create reports for data corresponding to the adverse event reports. A user interface is provided on a display to present to a user statistics, related reports, safety warnings, notices and related data based on all, or a subset of all, adverse event reports communicated to the end-user receiving parties by users generally.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

In embodiments, the invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and non-removable media implemented in any method or technology for storage of information, such as computer readable instructions, data structures, program modules, or other data. In this regard, computer storage media may include, but is not limited to, random access memory (RAM), read-only memory (ROM), electrically erasable programmable read-only memory (EEPROM), flash memory or other memory technology, compact disc read-only memory (CD-ROM), digital versatile disks (DVDs) or other optical disk storage, magnetic cassettes, magnetic tape, magnetic disk storage, or other magnetic storage device, or any other medium which can be used to store the desired information and which may be accessed by the server 102. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more internal computing devices 108 or external computing devices 110. Internal and external computing devices 108 and 110 are distinguished herein only to depict their relationship with respect to their physical location. Internal computing devices 108 are generally located at a variety of locations in a medical or research environment, for example, but not limited to, clinical laboratories, hospitals and other inpatient settings, veterinary environments, ambulatory settings, medical billing, quality control and financial offices, hospital administration settings, home health care environments, and clinicians' offices, while external computing devices 110 are generally located at a variety of locations exterior to the medical or clinical setting, such as, but not limited to government organizations, regulatory agencies, drug or device manufacturers, non-governmental health organizations, and research organizations, among others.

Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The computing devices 108 may also be physically located in non-traditional medical care environments so that the entire health care community may be capable of integration. The computing devices 108 may be personal computers, servers, routers, network PCs, peer devices, other common network nodes, or the like, and may include some or all of the components described above in relation to the server 102. The computing devices 108 can also be personal digital assistants or other like devices.

Exemplary computer networks 106 may include, without limitation, local area networks (LANs), wide area networks (WANs), and wireless local area networks (WLANS). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the computing devices 108. For example, and not by way of limitation, various application programs may reside on the memory associated with any one or more of the computing devices 108. It will be appreciated by those of ordinary skill in the art that the network connections shown are exemplary and other means of establishing a communications link between the computers (e.g., server 102 and computing devices 108) may be utilized.

In operation, a user may enter commands and information into the server 102 or convey the commands and information to the server 102 via one or more of the computing devices 108 through input devices, such as a keyboard, a pointing device such as a mouse, a trackball, or a touch pad. Other input devices may include, without limitation, microphones, satellite dishes, scanners, or the like. Commands and information may also be sent directly from a remote healthcare device to the server 102. In addition to a monitor, the server 102 and/or computing devices 108 may include other peripheral output devices, such as speakers and a printer.

Although many other internal components of the server 102 and the computing devices 108 are not shown, those of ordinary skill in the art will appreciate that such components and their interconnection are well known. Accordingly, additional details concerning the internal construction of the server 102 and the computing devices 108 are not further discussed herein.

Figure 2:
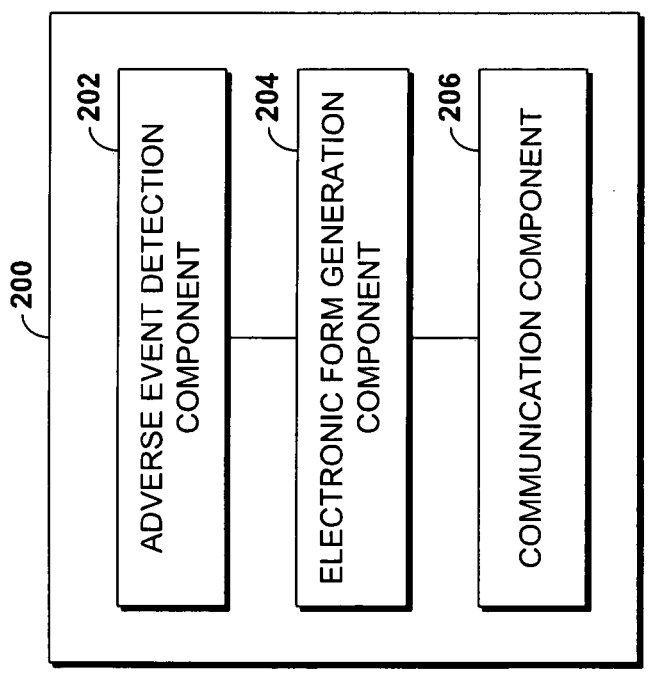
FIG. 2 is a block diagram of an exemplary computing system architecture suitable for use in implementing embodiments of the invention.

Referring now to FIG. 2, a block diagram of an exemplary computing system architecture 200 suitable for use in implementing embodiments of the invention is described. The system 200 may be comprised of an adverse event detection component 202, an electronic form generation component 204, and a communication component 206. The adverse event detection component 202 detects the occurrence of an adverse event manually or automatically. Manual detection of an adverse event is achieved by receiving an input from a user. Such an input may comprise a selection entered by a user on a computing device 108, such as through a click of a mouse at a display on the computing device having a selectable button, icon or other figure, among other methods.

Automatic detection of an adverse event is achieved by monitoring and analyzing a patient's electronic health record (EHR). Data entries to the EHR are monitored for data describing an adverse event using keywords or phrases. The data entries may also be analyzed to identify specified combinations or relationships between data points, such as, for example but not limitation, drug-to-drug, drug-to-symptom, and device-to-symptom interactions, among others. In an embodiment, rules are also provided to identify combinations and relationships of drugs, devices, symptoms, and events, as well as medication usage, patient clinical results, and user activities combined with patient clinical results, among others, that may indicate an adverse event occurrence. For example, data indicating that a patient was given the antihistamine diphenhydramine, which may be given to reduce allergic reactions, along with a notation that the patient had symptoms of an allergic reaction, or that the use of another drug has been discontinued, might imply the occurrence of an adverse event. Other combinations, relationships, or rules that are used to identify the occurrence of an adverse event are contemplated by the inventors and such are understood as disclosed herein.

Further, the monitoring and analysis includes data from a patient's entire EHR and medical history, not just the most recent data entries. In embodiments, this allows identification of adverse events having long latency periods between a cause and a resulting symptom. In such a case, it may be very difficult for a clinician to identify a drug or other cause of a symptom as such, because the cause may have occurred prior to the patient coming under the clinician's care, or distant enough in the past to be passed over at first blush as a possible cause of current symptoms, among other reasons.

Referring again to FIG. 2, the electronic form generation component 204 generates an electronic adverse event reporting form. The electronic form may be of any format or style and have any desired features. In embodiments, the electronic form has a format and data entry points similar to that found in an adverse event reporting form provided by a regulatory body or other government organization having authority over the medical field related to adverse event reports. For example, the electronic form may have fields and data points that correlate closely to an adverse event reporting form provided by the FDA MedWatch program, form FDA 3500 (10/05), or prior or subsequent versions thereof. The electronic form may further be provided in any electronic format including hypertext markup language (HTML), portable document format (PDF), or extensible markup language paper specification (XPS), among others, and may utilize browsing and viewing features such as tabs, pop-up windows, and drop down menus, among others. Many possible variations for creating, displaying, viewing and interacting with an electronic form may be used, all of which are contemplated by the inventors and are incorporated herein.

The form generation component 204 pre-populates one or more fields or data points of the electronic form with data from a patient's EHR. Data such as a patient's initials, age, date of birth, gender, and weight, among other demographic information are obtained from the patient's EHR and inserted into the electronic form. In embodiments, information regarding the adverse event is also pre-populated in the form. Such data may include, whether the event was an adverse event, product problem, product use error, outcome of the event, severity of the event, date of the event, and suspect product for the cause of the event, among others, if such information is available in the patient's EHR and is determinable by the form generation component 204.

The form generation component 204 also presents the electronic form on a display to a user to allow the user to verify any pre-populated data, make any necessary changes, and to add additional information in fields of the form where necessary.

The communication component 206 prepares the electronic form for communication to one or more desired end-user receiving parties. The communication component 206 may provide several functions prior to communicating the data in the form including validating the structure of the electronic form, encrypting, providing a signature on or in the electronic form file, and formatting the electronic form. Encryption of the electronic form may be completed by any method available in the art, and typically may comply with one or more standards for secure electronic interchange of drug safety information.

Formatting the electronic form provides any desired format for transmission of the data in the electronic form via a network 106 to one or more external computing devices 110 including integrating the electronic form in an electronic mail message to be communicated via a mail server or exchange server. Further, the formatting and communication of the data in the electronic form may be completed so as to comply with one or more standards or guidelines for communication of medical and pharmaceutical information. Such standards and guidelines include v2.x and v3.0 from Health Level Seven, Inc. (HL7), and E2B provided by the International Conference on Harmonization of Technical Requirements for Registration of Pharmaceuticals for Human Use (ICH), or previous and subsequent versions thereof, among others.

Upon receipt of the data in an electronic form by an end-user receiving party, the receiving party may access and use the electronic form by viewing the electronic form on a computing device display, printing a copy, and populating one or more databases with the data provided in the electronic form. Receipt of the data in an adverse event reporting form in electronic form may expedite and increase the efficiency of an end-user receiving party's processes of compiling data from one or more adverse event reports, processing cases corresponding to reports, and providing feedback to users that file reports, among other uses and advantages.

Figure 3:
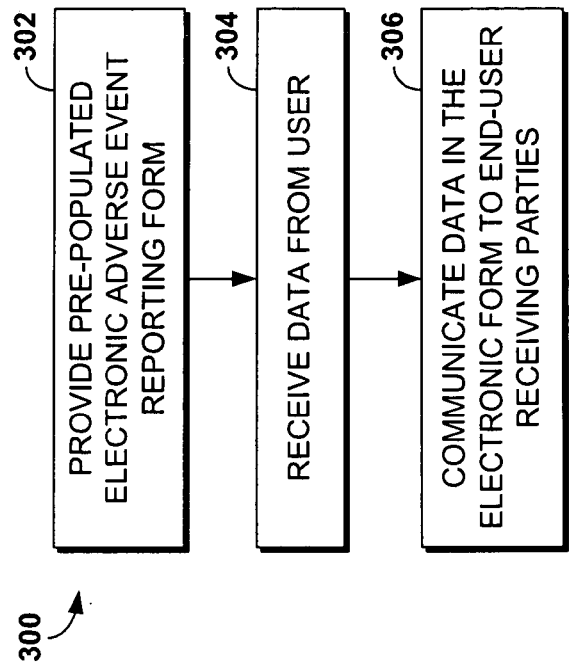
FIG. 3 is a flow diagram depicting a method in a clinical computing environment for communicating data in an electronic adverse event reporting form according to an embodiment of the invention.

With reference now to FIG. 3 a flow diagram depicting a method 300 in a clinical computing environment for communicating data in an electronic adverse event reporting form according to an embodiment of the invention is described. At block 302, an electronic adverse event reporting form is presented to a user, the form having been pre-populated with one or more data obtained from a patient's EHR. A user provides additional data to the electronic form and/or reviews and edits any pre-populated data, at block 304. The data in the electronic form are communicated to one or more end-user receiving parties such as, for example, but not limitation, a government organization, a regulatory agency, a manufacturer, a non-governmental health organization, a research organization, a quality control department or personnel, or other interested parties, at block 306.

Figure 4:
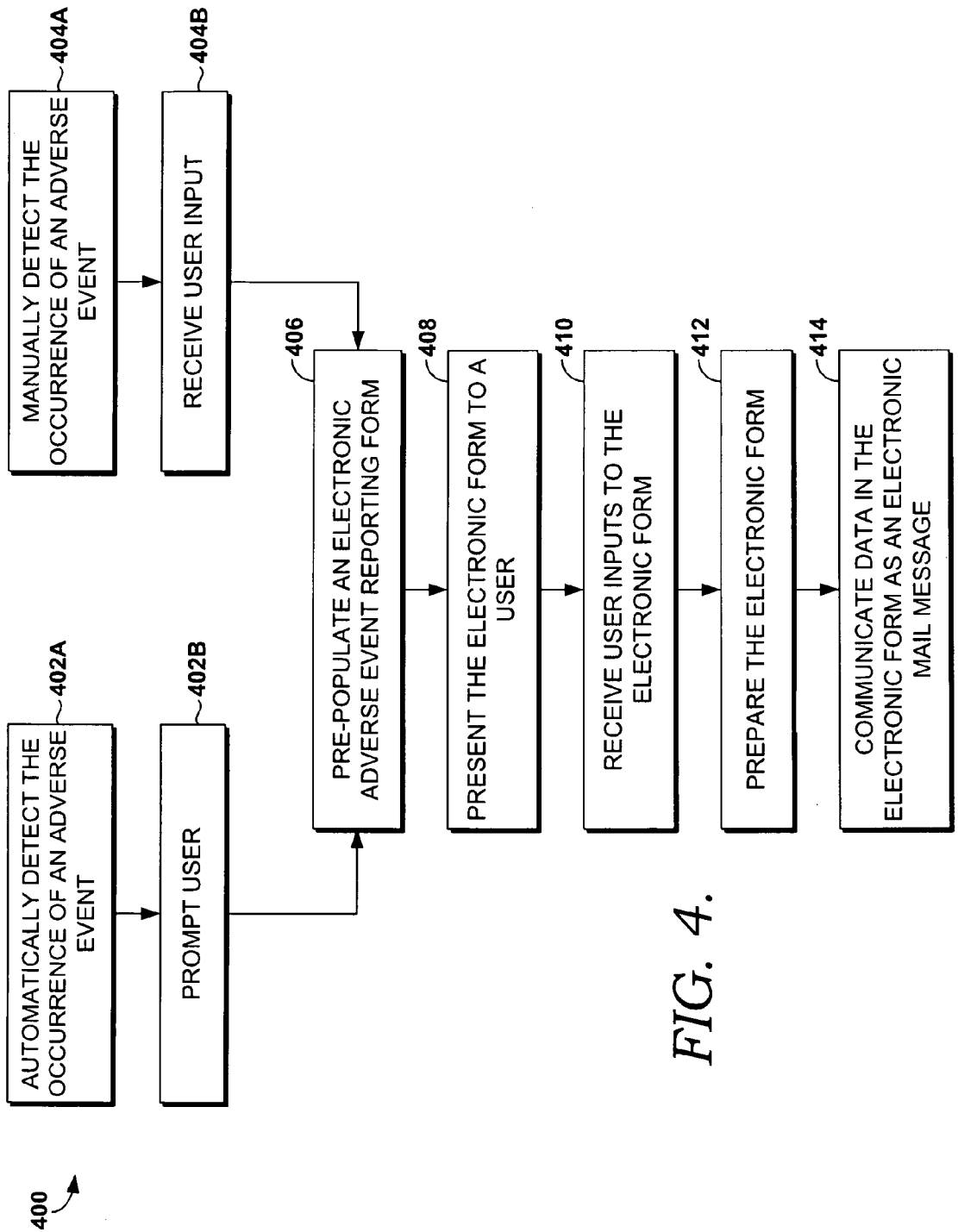
FIG. 4 is a flow diagram depicting a method in a clinical computing environment for communicating data in an electronic adverse event reporting form according to an embodiment of the invention.

Referring now to FIG. 4, a flow diagram depicting a method 400 in a clinical computing environment for communicating data in an electronic adverse event reporting form according to an embodiment of the invention is described. Initially, an adverse event is automatically detected (402A) and a user prompted to report the adverse event, at block 402B. The automatic detection of the adverse event at block 402A may be completed by monitoring and analyzing a patient's EHR and entries thereto, as described above. The prompt provided to the user at block 402B may have visual, audio, or both components that are displayed to a user at a computing device, such as the computing device 108, upon detection of an adverse event occurrence by the system, such as the system 200. The prompt notifies the user of the possible occurrence of an adverse event and provides one or more data that produced the detection of a possible adverse event occurrence. Upon receiving the prompt, a user may provide an input to the system 200 at the computing device 108 to indicate an intention to report the detected adverse event. The user's input can be provided by any method described above, such as for example, providing a selection via a mouse, or touching an active field of a touch screen display, among others. Alternatively, where reporting of an adverse event is voluntary or where a false detection is made, among other instances, a user may elect not to report the detected adverse event occurrence by providing an input to the computing device 108 in a similar manner as described previously.

An alternative method for detecting an adverse event occurrence is provided at block 404A in which a user manually detects an adverse event. Where a user wishes to report a manually detected adverse event, the user provides an input (404B) to the computing device by any method described above such as, for example, selecting an adverse event reporting field, button, icon, or other feature displayed as a component in a display of a patient's EHR, among other locations.

Upon election to report an adverse event at blocks 402B or 404B, an electronic adverse event reporting form is at least partially pre-populated with one or more data from a patient's EHR, as depicted by block 406. The pre-populated electronic form is presented to a user (408) for review, or alteration of the pre-populated data and entry of additional data (410). The electronic form, with pre-populated and user entered data, is then prepared for communication, transmission or, submission by formatting, verifying, encrypting and signing, as described above (412), and the data communicated to one or more end-user receiving parties as an electronic mail message among other methods, as shown at block 414.

Figure 5:
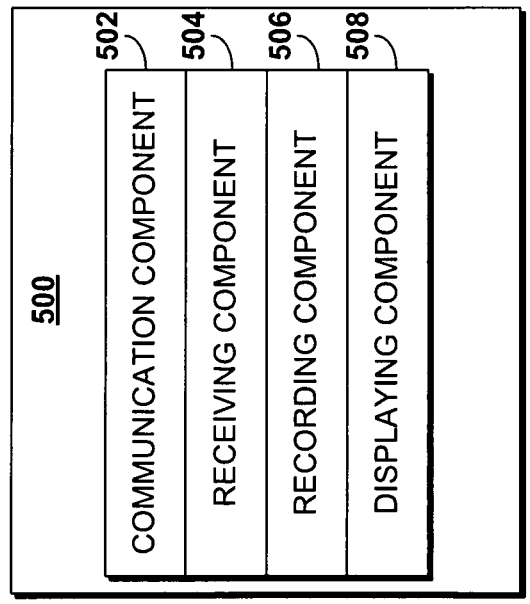
FIG. 5 is a block diagram of an exemplary computing system architecture suitable for use in implementing embodiments of the invention.

With reference now to FIG. 5, a system 500 in a clinical computing environment for facilitating the tracking of one or more adverse event reports is described. The system 500 comprises a communication component 502, a receiving component 504, a recording component 506, and a displaying component 508. The communication component 502 provides the same functions and operations as described above for the communication component 206 including preparing an electronic form for communication to one or more desired recipients, validating the structure of the electronic form, encrypting the electronic form, providing a signature on, or in, the electronic form file, and formatting the electronic form.

The receiving component 504 receives one or more of an acknowledgment receipt, a successful transmission receipt, a transmission failure receipt, and a unique identifier, among others receipts and identifiers, from one or more end-user receiving parties to whom data in an electronic adverse event reporting form is communicated by the communication component 504. An acknowledgement receipt received by the receiving component 502 may comprise any signal, indication, or other notification from an end-user receiving party computing device 110 indicating acknowledgement of receipt of an electronic form communication. In embodiments, the acknowledgement receipt comprises an ACK acknowledge character or acknowledgement code.

The receiving component 504 may also receive a successful transmission receipt or a transmission failure receipt from one or more of the end-user receiving parties to indicate the success or failure of the communication of an electronic adverse event reporting form. In embodiments, a successful transmission receipt comprises a message disposition notification (MDN) message that indicates to a user the successful transmission and receipt of the electronic form by a receiving party, and contains a receipt number for the submission transaction for the electronic report. A transmission failure receipt may comprise a bounce message, delivery status notification (DSN) message, a non-delivery report (NDR), a non-delivery notification (NDN), or a bounce. Where a transmission failure receipt is received, the user or the system 500 may retry the communication if desired.

Further, the receiving component 504 may receive a unique identifier for the adverse event report submitted as an electronic form. The unique identifier may be assigned and supplied by an end-user receiving party and may be used to track the status or disposition of a case associated with an adverse event report, among other uses. The unique identifier may be communicated as, or with an MDN, among other forms of notification.

With continued reference to FIG. 5, the recording component 506 functions to record one or more of the acknowledgment receipts, successful transmission receipts, transmission failure receipts, and unique identifiers in one or more records associated with the adverse event report. The receipts and identifiers may be recorded by simply placing a numeric, alpha-numeric, or other character or character string in a record. The receipts or identifiers may also be recorded by inserting or attaching an electronic file, or link to an electronic file containing the receipts or identifiers in the records. The character, character string or file may be configured to allow a user to track, retrieve, and view, among other operations, information associated with the receipt or identifier such as the time and date of communication and the sender and recipient. Further, the recordation is made in any desired electronic record including a patient's EHR, quality control records, and a clinician's records, among others.

The displaying component 508 provides one or more user interfaces on a computing device 108 at which a user accesses, views, sorts, audits, and creates reports, among other operations, for submitted adverse event reports. The user may be provided with access and interaction with adverse event reports communicated by the user, by a group of users, or by all users. The user may also be provided with status information for one or more reports. The status information may include whether the regulatory body has accessed, processed, filed, or otherwise handled the report. Further, the user may be provided with one or more statistics, related reports, safety warnings, notices, and related data based on all, or a subset of all adverse event reports submitted to the one or more end-user receiving parties.

In embodiments, the user interfaces provided by the displaying component 508 comprise any desired format including, but not limited to windows, webpages, tabbed pages, viewing panes, pop-up menus, drop-down menus, and scroll-out pages, among others. The user interfaces provide links, shortcuts, hyperlinks, icons, buttons, and files, among others to allow a user to access adverse event reports, related cases, related information, websites, functions and tools, among others. One of skill in the art may recognize other formats, components, tools, and functions, among others, that may be used to provide a user interface as described herein, all of which are hereby incorporated herein.

Figure 6:
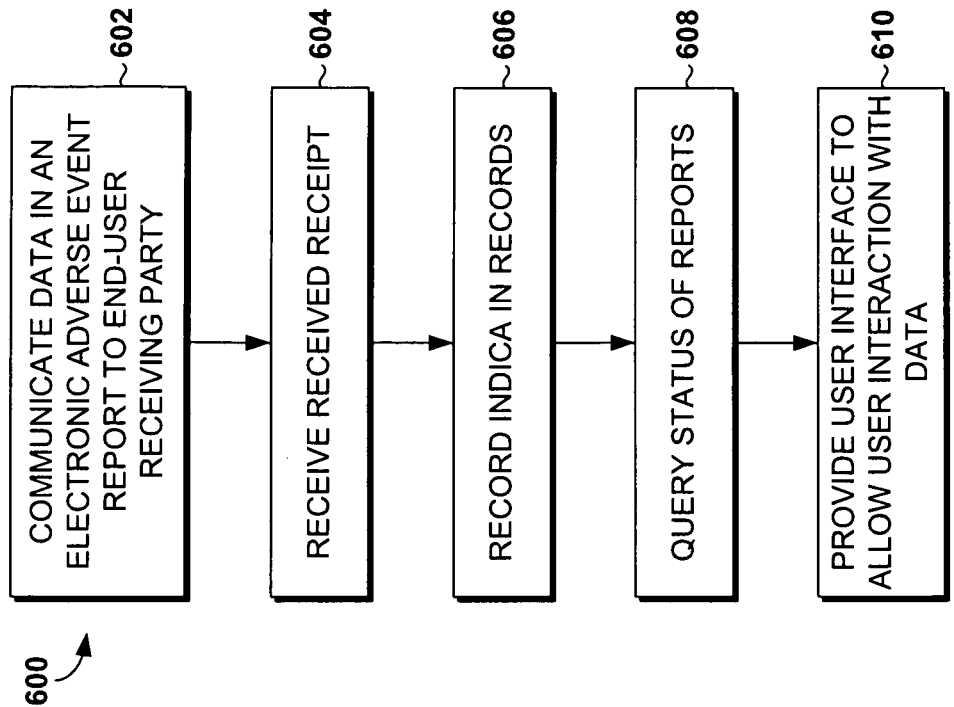
FIG. 6 is a flow diagram depicting a method in a clinical computing environment for tracking one or more adverse event reports according to an embodiment of the invention.

Referring now to FIG. 6, a flow diagram depicting a method 600 in a clinical computing environment for tracking one or more adverse event reports according to an embodiment of the invention is described. Initially, data in an electronic adverse event reporting form are communicated to an end-user receiving party as described previously, at block 602. One or more receipts depicting receipt of the electronic form as described above are received at block 604 and are recorded to one or more records at block 606. At block 608, a user queries the status of one or more adverse event reports, and data corresponding to the one or more reports are displayed at a user interface for user interaction at block 610.

In an embodiment, to query the status of adverse event reports, a system communicates with the end-user receiving party via a network. The system uses indicia from the one or more receipts, such as a tracking number, to query the status of an associated report. One or more systems or computing devices of the end-user receiving party responds with status information and other related information that is then displayed to a user.

Figure 7:
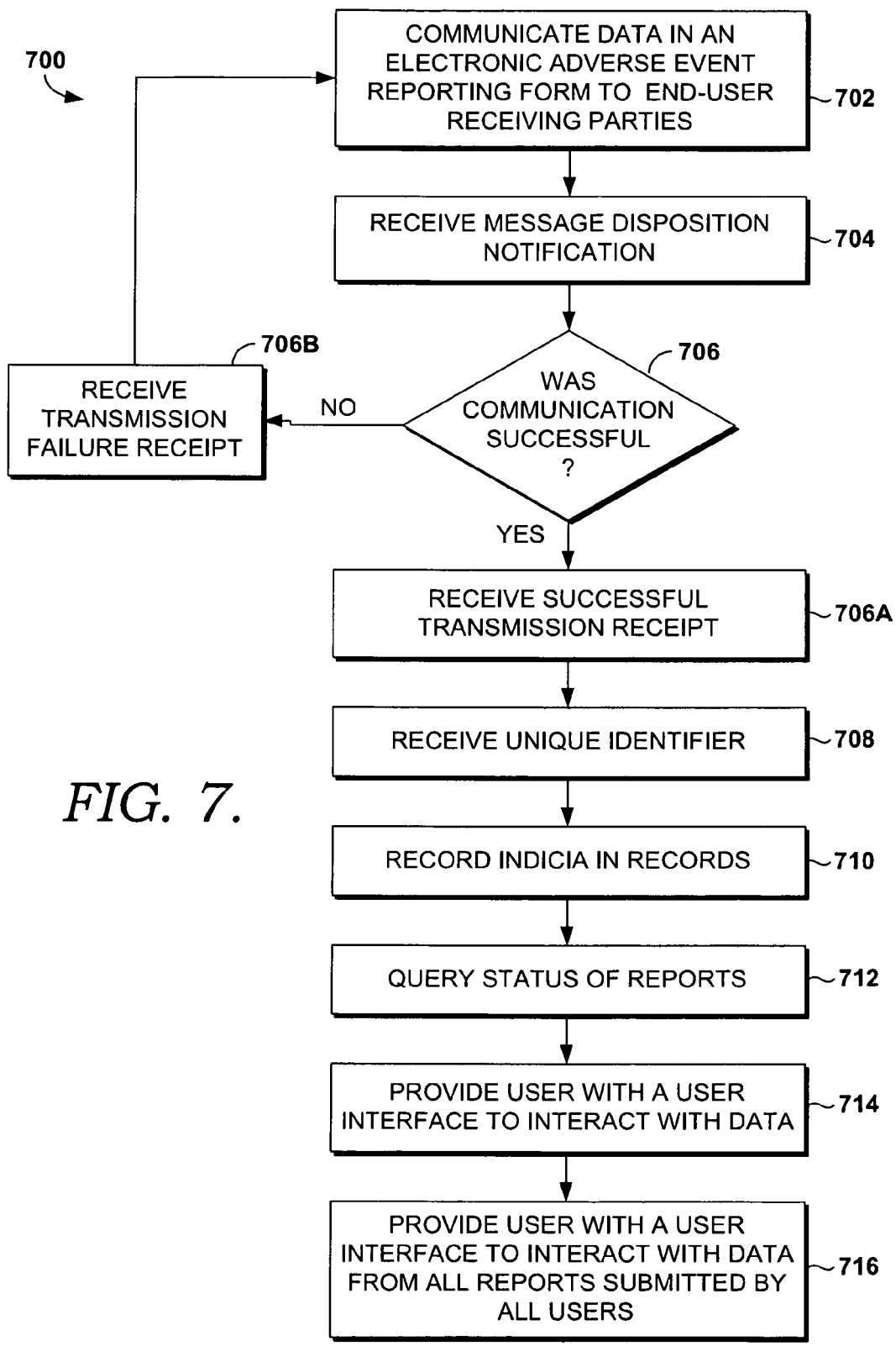
FIG. 7 is a flow diagram depicting a method in a clinical computing environment for tracking one or more adverse event reports according to an embodiment of the invention.

With reference to FIG. 7, a flow diagram depicting a method 700 in a clinical computing environment for tracking one or more adverse event reports according to an embodiment of the invention is described. Data in an electronic adverse event reporting form are communicated to an end-user receiving party at block 702, and an MDN such as described previously, is received at block 704. If the communication of the electronic form fails at block 706, then a transmission failure receipt is received at block 706B and the process returned to block 702 to again attempt to communicate an electronic form to an end-user receiving party. If the communication of the electronic form is successful at block 706, then a successful transmission receipt, such as an MDN message, among others, is received at block 706A. A unique identifier, such as a tracking number, is received as an MDN message or in an MDN message at block 708, among other methods and identifiers. Indicia for the successful transmission receipt and unique identifiers are recorded in one or more records, including, for example, a patient's EHR, a hospital's quality control records, or a clinician's records, among others, at block 710.

At block 712, a user queries the status of one or more adverse event reports that the user has submitted, or may query the status of reports submitted by an associated group of users. The user is provided with one or more user interfaces in which to view, sort, audit, and create reports, among other operations, for the queried adverse event reports (714). The user also obtains information related to adverse event reports submitted by all users to the regulatory body at a user interface provided at block 716.

Figure 8:
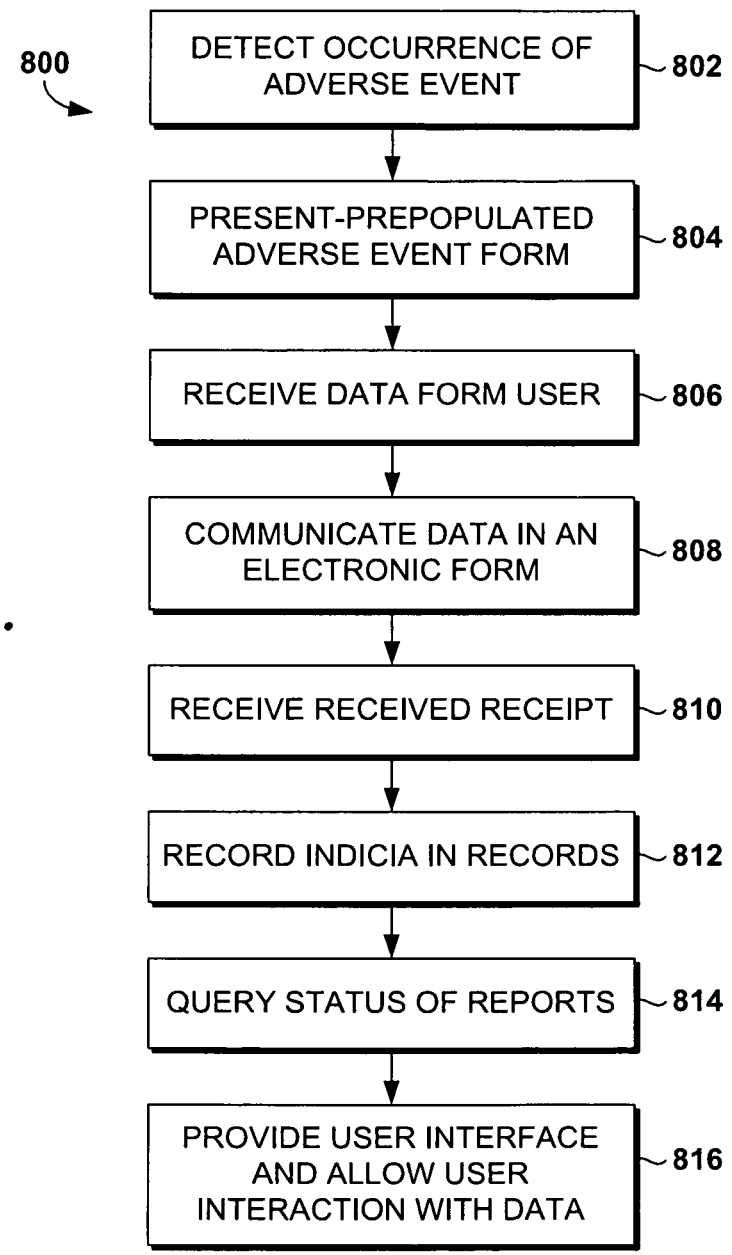
FIG. 8 is a flow diagram depicting a method in a clinical computing environment for communicating data in an electronic adverse event reporting form and tracking one or more adverse event reports according to an embodiment of the invention.
Figure 10:
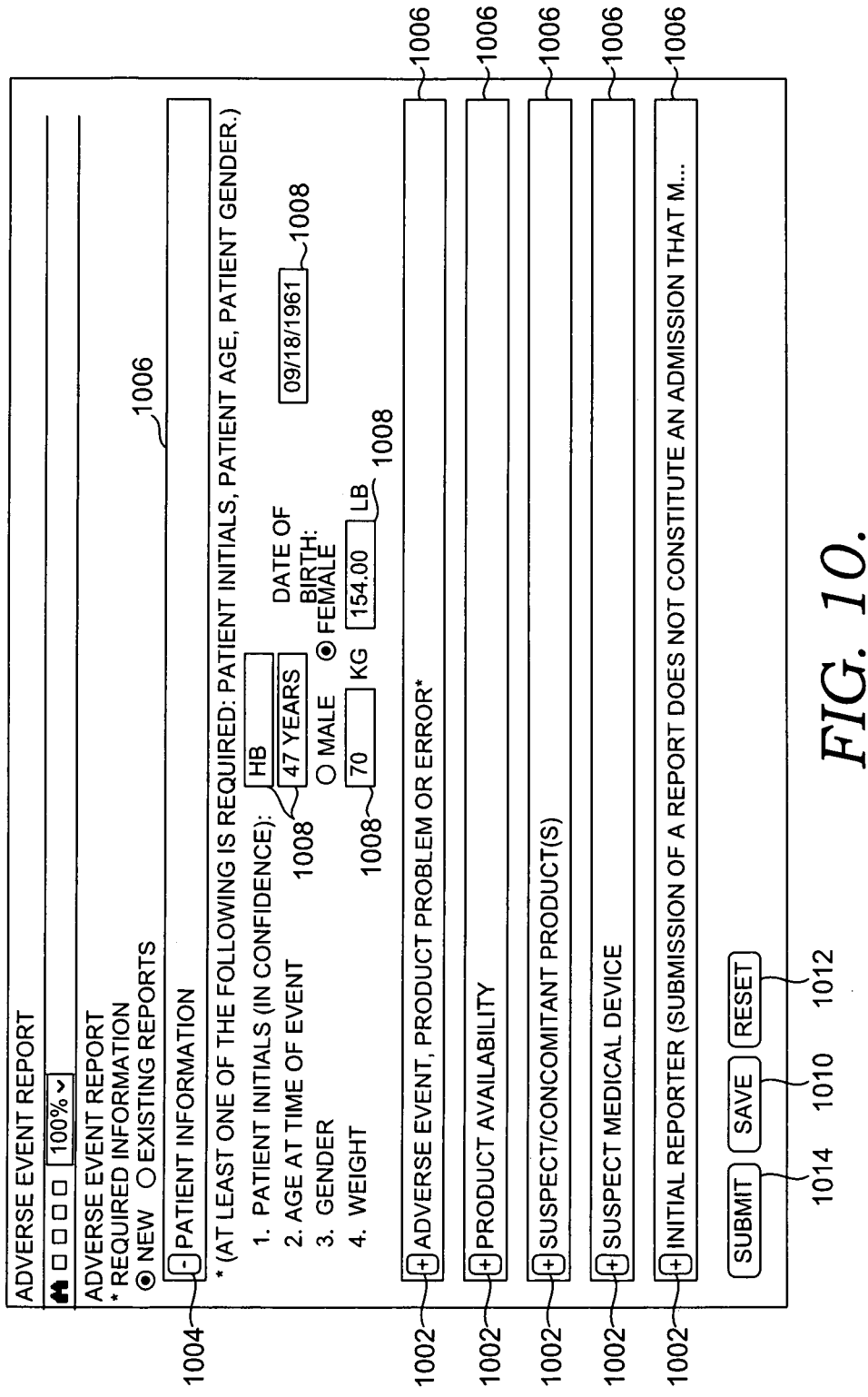
FIG. 10 is a graphical representation of a patient information section of an electronic adverse event reporting form according to an embodiment of the invention.

With reference now to FIGS. 8-14 an example of a method 800 for communicating and tracking adverse event reports is described according to an embodiment of the invention. Referring initially to FIG. 8, a flow diagram depicting a method 800 in a clinical computing environment for communicating data in an electronic adverse event reporting form and tracking one or more adverse event reports according to an embodiment of the invention is depicted. Preliminarily, a patient enters a health care system and an EHR is created. Clinicians update the patient's EHR as symptoms are presented, diagnoses are made, and drugs or other care is provided, among other recorded events. A system, such as the system 200, monitors and analyzes one or more data entries to the patient's EHR as the record is updated. At block 802, an adverse event is detected by the system either automatically or manually where the monitoring and analysis, or a clinician, indicate the occurrence of an adverse event. The system then presents an electronic adverse event reporting form, as illustrated in FIG. 9, pre-populated with one or more data from the patient's EHR, at 804. The electronic form provides one or more expandable fields for ease of viewing and entry of adverse event information, as shown in FIG. 9 and is accessed from the patient's EHR and/or from a separate access point. The pre-populated data in the electronic form includes patient information as shown in FIG. 10, which depicts an expanded Patient Information section having pre-populated and editable data fields.

The system may receive one or more data from a clinician, or other user, at editable fields in a Patient Information section 1102 as described above, or in an Adverse Event, Product Problem or Error section (FIG. 11), a Product Availability section 1202 (FIG. 12), a Suspect/Concomitant Product(s) section 1204 (FIG. 12), a Suspect Medical Device section 1302 (FIG. 13), and an Initial Reporter section 1304 (FIG. 13), among other sections. In embodiments, each of the sections may be expanded and collapsed as desired by a user through use of a plus or minus icon near a section title bar for each section, among other methods. The user may enter any necessary or known data in available fields by selecting an appropriate field and entering the data through the use of a keyboard or other input device, and may save, cancel, or submit the data in the electronic form by selecting an appropriate icon or button depicted along the bottom of the sections in FIG. 9, among other methods and operations.

Upon completion of all necessary data entry and receipt of a submit command from the user as described above, the system, such as systems 200 and 500, communicates the data directly to one or more end-user receiving parties, such as regulatory bodies, government agencies, manufacturers, non-governmental health organizations, research groups, or other interested parties.

Communication of the data to the above described bodies may be completed by any available method including submission as an electronic mail (email) message via a mail exchange server, such as server 102, among others. The system may be provided with a list and/or database of recipients and their network addresses or email addresses for each product, drug, device, or other component that may cause or be involved in an adverse event occurrence. In embodiments, the system determines the bodies to which adverse event data should be submitted from the data provided by the user and/or a user is provided with a list from which to select recipients, among other methods.

Having received a command to submit the electronic form and selected appropriate recipients, the system formats the electronic form as an email message or inserts the electronic form into an email message. The system also validates the electronic form for content, and format, among other characteristics, and encrypts and signs the message. The electronic form and/or the associated email message is further formatted to comply with one or more standards for electronic transmission of healthcare data such as HL7 v2.x, v3.0, or ICH E2B, among others. The data are then communicated to the selected end-user receiving parties as depicted at block 808.

At block 810, a system, such as system 500, receives one or more received receipts from one or more of the one or more selected end-user receiving parties. The received receipts indicate an acknowledgement of the transmission of the electronic form, successful transmission, or a failed transmission, and may include a unique identifier such as a tracking number from a receiving party, among others. The receipts may be received from each of the receiving parties, or from only a few, or one, such as only from a regulatory agency. Indicia for one or more of the receipts are recorded in one or more records associated with the adverse event report including a patient's EHR, a healthcare system's quality control records, and a clinician's records, among others, at 812.

A clinician, researcher, or other user uses the system to query or view the status of the submitted adverse event report, as depicted at block 814. The status of other reports submitted by the user, by a group of users, or by all users may also be queried or viewed. A user interface for interacting with results from the query is provided by the system as depicted in FIG. 14, and at 816. In an embodiment, the user interface provides a listing of patient names, adverse event descriptions, and other pertinent information 1402, as well as icons 1404 or buttons providing access to additional information. The user interface is generally provided at an access point separate from a patient's EHR and requires a user's name and a password or may use another security procedure. The user interface allows a user to sort the query results by date, patient name, advisor type, and advisor status, among others. The user interface also allows the user to view, access, audit, and prepare reports, among other functions, for the one or more adverse event reports.

The user interface also provides additional information to a user following submission of an adverse event report, following a query, or at another interaction point. The additional information may include information or statistics related to similar reported adverse events, other events of importance, safety warnings, and notices, among other information that may be made available. The information may be provided at a separate section of a user interface, as a pop-up window, or as an email to the user, among other methods.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A method in a medical information computing environment for communicating data in an electronic adverse event reporting form directly to one or more end-user receiving parties, the method comprising:
    monitoring, by a computing device having a processor and a memory, an electronic health record of a patient for one or more keywords that indicate the occurrence of an adverse event;
    detecting by the computing device the occurrence of the adverse event based on the presence of the keywords in the electronic health record of the patient;
    presenting automatically on a display device an electronic adverse event reporting form pre-populated with one or more patient data obtained from the electronic health record of the patient;
    receiving one or more additional data from a user; and
    electronically communicating, by the computing device having a processor and a memory, the data in the electronic form to the one or more end-user receiving parties, wherein the one or more end-user receiving parties comprise one or more of a government organization, a regulatory agency, a manufacturer, a non-governmental health organization, a research organization, quality control personnel, and an interested party.

2. The method of claim 1, wherein the electronic form is substantially similar in content to an adverse event reporting form provided by one or more of a government organization, a regulatory agency, a non-governmental health organization, and a research organization.

3. The method of claim 2, wherein the content of the electronic form is substantially similar to an adverse event reporting form provided by the United States Food and Drug Administration.

4. The method of claim 1, wherein the one or more data in the electronic form are communicated directly to at least the United States Food and Drug Administration.

5. The method of claim 1, wherein the one or more data in the electronic form are formatted to comply with an industry standard format.

6. The method of claim 5, wherein the one or more data in the electronic form are formatted to comply with at least one of a Health Level Seven, Inc. (HL7) standard and International Conference on Harmonization of Technical Requirements for Registration of Pharmaceuticals for Human Use (ICH) guidelines.

7. The method of claim 1, wherein the one or more data in the electronic form are communicated as an electronic mail message.

8. The method of claim 7, wherein one or more of validating, encrypting and signing the message are completed prior to the step of communicating.

9. The method of claim 1, wherein the one or more data in the electronic form are usable by the one or more end-user receiving parties for at least one of viewing the electronic form on a computing device display, printing a copy of the electronic form, and populating one or more databases with the one or more data in the electronic form.

10. The method of claim 1, wherein a user accesses the electronic form from a user interface on a computing device displaying a patient's electronic health record.

11. The method of claim 1, wherein the user is automatically prompted with the electronic form at a user interface of a computing device when an adverse event is detected.

12. A system in a medical information computing environment for facilitating the direct communication of one or more data in an electronic adverse event reporting form to one or more end-user receiving parties, the system comprising:
one or more computing devices having a processor and a memory and configured to provide:
an adverse event detection component that detects an adverse event through monitoring and analyzing a patient's one or more electronic health records to identify a combination of first data elements in the one or more electronic health records that indicate the occurrence of the adverse event;
an electronic form generation component that generates an electronic form, at least partially pre-populates the form with one or more second data elements from patient's one or more electronic health records, the second data elements being the same or different than the first data elements, and presents the at least partially pre-populated form to a user to allow additional input of one or more third data elements; and
a communication component that electronically communicates the one or more second and third data elements in the electronic form directly to the one or more end-user receiving parties.

13. The system of claim 12, wherein the content of the electronic form is substantially similar to an adverse event reporting form provided by the United States Food and Drug Administration.

14. The system of claim 12, wherein the electronic form is formatted to comply with one or more of a Health Level Seven, Inc. (HL7) standard and International Conference on Harmonization of Technical Requirements for Registration of Pharmaceuticals for Human Use (ICH) guidelines.

15. The system of claim 12, wherein the one or more data in the electronic form is communicated as an electronic mail message directly to the one or more end-user receiving parties, and wherein the end-user receiving parties comprise one or more of a government organization, a regulatory agency, a non-governmental health organization, a research organization, and an interested party.

16. The system of claim 15 wherein the communication component provides one or more of the functions of validating the structure of the message, validating the one or more data, encrypting the message, encrypting the data, and signing the message prior to communicating the message.

17. A method in a medical information computing environment for communicating one or more data in an electronic adverse event reporting form directly to one or more end-user receiving parties, the method comprising:
monitoring, by a computing device having a processor and a memory, a patient's electronic health record for a combination of first data elements that display a relationship between one or more of drugs, symptoms, and devices used in the care of the patient, the relationship indicating the occurrence of an adverse event, the adverse event comprising one or more of a medical error and an adverse reaction to a treatment provided to the patient;
detecting, by the computing device having a processor and a memory, the occurrence of the adverse event based on the combination of first data elements;
pre-populating an electronic adverse event reporting form with one or more second data elements from the patient's electronic health record, the first and second data elements being the same or different;
presenting the electronic form to a user on a display device;
receiving one or more additional third data elements from a user to the electronic form;
preparing the one or more second and third data elements in the electronic form for communicating to at least the United States Food and Drug Administration by formatting the electronic form in an electronic messaging format in compliance with at least one of a Health Level Seven, Inc. (HL7) standard and International Conference on Harmonization of Technical Requirements for Registration of Pharmaceuticals for Human Use (ICH) guidelines, and providing one or more of validation, encryption and signing of one or more of the message and the one or more second and third data elements in the electronic form; and
communicating the one or more second and third data elements in the electronic form to at least the United States Food and Drug Administration as an electronic mail message.

* * * * *